US008160706B2

(12) United States Patent
Kelly et al.

(10) Patent No.: US 8,160,706 B2
(45) Date of Patent: Apr. 17, 2012

(54) PHASED DEACTIVATION OF FUNCTIONALITY IN IMPLANTABLE MEDICAL DEVICE SYSTEMS

(75) Inventors: Jonathan H. Kelly, Woodbury, MN (US); James O. Kalgren, Lino Lakes, MN (US); Gang Wu, Blaine, MN (US); James O. Gilkerson, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 672 days.

(21) Appl. No.: 12/259,458

(22) Filed: Oct. 28, 2008

(65) Prior Publication Data
US 2009/0157144 A1    Jun. 18, 2009

Related U.S. Application Data

(60) Provisional application No. 61/013,748, filed on Dec. 14, 2007.

(51) Int. Cl.
*A61N 1/37* (2006.01)

(52) U.S. Cl. .......................... 607/32; 607/31

(58) Field of Classification Search .................. 607/32, 607/59, 31
See application file for complete search history.

(56) References Cited

U.S. PATENT DOCUMENTS

| 4,562,841 | A | 1/1986 | Brockway et al. |
| 6,424,867 | B1 | 7/2002 | Snell et al. |
| 6,993,393 | B2 * | 1/2006 | Von Arx et al. ............... 607/60 |
| 2006/0089684 | A1 * | 4/2006 | Blaha et al. .................. 607/60 |

* cited by examiner

*Primary Examiner* — Michael Kahelin
(74) *Attorney, Agent, or Firm* — Pauly, Devreis, Smith & Deffner, L.L.C.

(57) ABSTRACT

Embodiments of the invention are related to systems for interfacing with implantable medical devices, amongst other things. In an embodiment, the invention includes an external medical system including a processor and a telemetry circuit in communication with the processor, the processor configured to communicate with an implanted medical device. The system can be configured to query a system user after a first period of time in which indicators of system use are not detected. The system can be further configured to deactivate one or more data transmission features of the implanted medical device after a second period of time in which one or more indicators of system use are not detected. Other embodiments are also included herein.

13 Claims, 7 Drawing Sheets

PHASED DEACTIVATION OF FUNCTIONALITY IN IMPLANTABLE MEDICAL DEVICE SYSTEMS

This application claims the benefit of U.S. Provisional Application No. 61/013,748, filed Dec. 14, 2007, the content of which is herein incorporated by reference.

TECHNICAL FIELD

This disclosure relates generally to medical devices and, more particularly, to systems for interfacing with implantable medical devices, amongst other things.

BACKGROUND OF THE INVENTION

Implantable medical devices are commonly used to treat patients with various conditions. By way of example, conditions of the heart such as tachycardia, bradycardia, and heart failure, amongst others, are now routinely treated using implantable cardiac rhythm management (CRM) devices. In addition, various conditions such as epilepsy, chronic pain, Parkinson's Disease, and depression can now be treated using implantable neurostimulation devices.

Patients with such implantable devices may periodically visit clinicians for follow-up appointments. During these follow-up appointments, clinicians may perform tasks such as adjusting the therapy settings of the implanted device in addition to accessing and reviewing data gathered by the device. In order to perform these tasks, the clinician will typically use an external device, such as a programmer-recorder-monitor (PRM) device in order to interrogate the implanted medical device and reprogram it if necessary.

When programming and data acquisition activities are complete, the interrogation session between the implanted device and the PRM device can be terminated. Session termination generally requires some affirmative action on the part of the operator of the PRM device.

SUMMARY OF THE INVENTION

Embodiments of the invention are related to systems for interfacing with implantable medical devices, amongst other things. In an embodiment, the invention includes an external medical system including a processor and a telemetry circuit in communication with the processor, the system configured to communicate with an implanted medical device. The system can be configured to query a system user after a first period of time in which one or more indicators of system use are not detected. The system can be further configured to deactivate one or more data transmission features of the implanted medical device after a second period of time in which one or more indicators of system use are not detected.

In an embodiment, the invention includes a processor and a telemetry circuit in communication with the processor configured to communicate with an implanted medical device. The system can be configured to query a system user regarding the identity of the patient after a first period of time in which one or more indicators of system use are not detected. The system can be configured to deactivate transmission of real-time data from the implanted medical device after a second period of time in which one or more indicators of system use are not detected. The system can also be configured to deactivate long-range telemetry functionality of the implanted medical device after a third period of time in which one or more indicators of system use are not detected.

In an embodiment, the invention includes a medical system including an implanted medical device and an external interface device for interacting with the implanted medical device. The external device can include a telemetry circuit for communicating with the implanted medical device. The external interface device can be configured to query a system user regarding the identity of the patient after a first period of time in which activity is not detected. The medical system can be configured to deactivate transmission of real-time data after a second period of time in which activity is not detected and deactivate long-range telemetry functionality after a third period of time in which activity is not detected.

In an embodiment, the invention includes a method of operating an external medical system including querying a system user after a first period of time in which the system has not received user input; and deactivating one or more features of an implantable medical device after a second period of time in which the system has not received user input.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

When programming and data acquisition activities of an interrogation session are complete, the interrogation session between the implanted device and the PRM device can be terminated. Session termination generally requires some affirmative action on the part of the operator of the PRM device.

However, in some circumstances, the operator may forget to take the required affirmative action to terminate the programming session. When this happens, confusion may develop. For example, when the next patient is seated for device interrogation the PRM device may still be communicating with the implanted medical device in the last patient seen. As such, the operator may believe the data shown on the PRM device reflects the patient seated in front of them, while the data actually reflects the previous patient.

In addition, implanted medical devices generally have a finite amount of battery-stored energy. When the battery-stored energy is used up, the device must generally be replaced through a costly surgical procedure. As such, conservation of energy stored by the device is a high priority.

In this regard, it should be noted that some of the communication features that are active during interrogation sessions can use up significant amounts of the implanted device's energy. For example, many implanted devices include a feature that allows them to transmit real-time data to an external medical device such as a programmer-recorder-monitor (PRM) device or an advanced patient management (APM) device. Transmission of this data in real-time can be useful for a clinician because they can observe many aspects of the patient's condition. However, transmission of this data in real-time can also use up a significant amount of energy. Another communication feature that is frequently active during device interrogation is radio-frequency (RF) communication. RF communication with an implanted device can offer advantages over more traditional inductive-based communication schemes including an enhanced range of data transmission. However, keeping RF communication turned on can also use up a substantial amount of the implanted device's energy.

Embodiments of the invention can help avoid these issues by appropriately querying the system user and disabling features in a phased approach in response to a lack of user activity. As such, embodiments of the invention can help to reduce operator confusion and conserve the energy of the implanted device.

Figure 1:
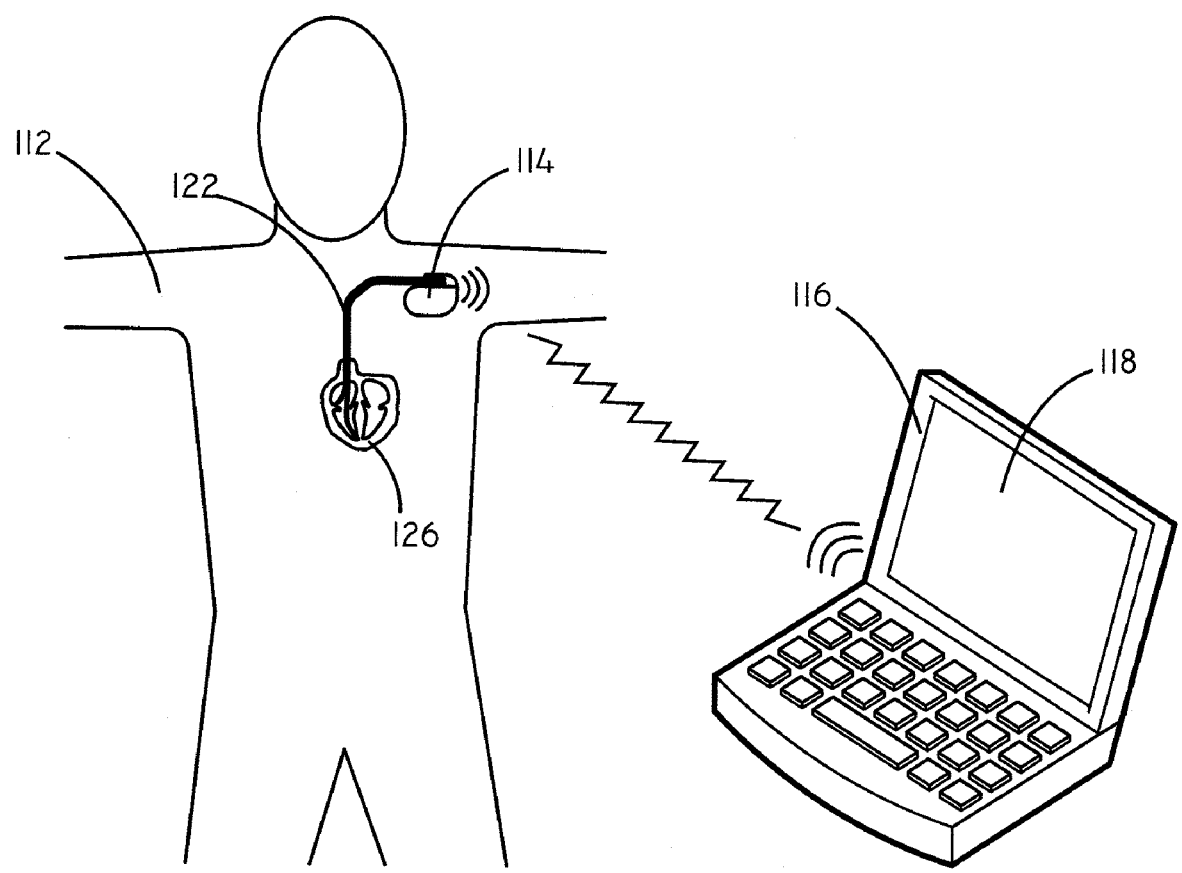
FIG. 1 is a schematic diagram of an example implementation, consistent with at least one embodiment of the technology disclosed herein.

FIG. 1 is a schematic diagram of an example implementation, consistent with at least one embodiment of the invention. An implantable medical device 114 is disposed within a patient 112. Exemplary implantable medical devices can include, but are not limited to, implantable cardiac rhythm management devices (including pacemakers, cardiac resynchronization therapy (CRT) devices, remodeling control therapy (RCT) device, cardioverter/defibrillators, or pacemaker-cardioverter/defibrillators, and the like), neurological stimulators, implantable sensors, and the like. One example of a cardiac rhythm management device is disclosed in commonly assigned U.S. Pat. No. 4,562,841, the content of which is herein incorporated by reference. The implantable medical device 114 can be in communication with one or more stimulation leads 122 that are positioned within proximity of the patient's heart 126. The implantable medical device 114 can be in communication with an external medical system 116. In some embodiments, the implantable medical device 114 can be in wireless communication with the external medical system 116. The external medical system 116 can include a telemetry circuit (not shown in FIG. 1) to facilitate communication with the implanted medical device 114.

Various types of wireless technologies can be used in order to facilitate communication between the external medical system 116 and the implantable medical device 114. By way of example, communication can be carried out through induction, radiofrequency (RF) transmission, acoustically, or the like. In contrast to induction, RF transmission generally allows for a greater range of transmission and does not required the use of a wand device to be placed directly over the site of the patient where the implanted device is located. However, RF communication consumes a significant amount of energy. As described below, RF communication between the implantable medical device 114 and the external medial system 116 can be deactivated in accordance with various embodiments herein in order to conserve the energy of the implantable medical device 114.

The implantable medical device 114 can be configured to gather data and transmit data to the external medical system 116. For example, the implantable medical device 114 can include sensors and gather data such as heart rate data, electrogram data, pressure data, volume data, flow rate data, temperature data, chemical analyte data, activity data, and accelerometer data. The implantable medical device 114 can transmit real-time data to the external medical system 116. In some embodiments, the external medical system 116 can display the real-time data through a video output 118. As described below, real-time transmission of data from the implantable medical device 114 to the external medical system 116 can be deactivated in order to conserve the energy of the implantable medical device 114.

The external medical system 116 can also transmit commands to the implantable medical device 114 in order to control its functioning. By way of example, the external medical system 116 can send commands to the implantable medical device in order to program its pacing mode, stimulation amplitude, stimulation timing, sensing parameters, and the like.

The external medical device 116 can be any type of device or combination of devices capable of interrogating the implantable medical device 114. In many embodiments, the external medical system 116 is a PRM device. Exemplary programmer/recorder/monitor devices include the Model 3120 Programmer available from Boston Scientific Corporation, Natick, Mass. However, it will be appreciated that the external medical system 116 can also take on other forms such as an in-home monitoring system or advanced patient management system. An exemplary in-home monitoring system is the LATITUDE® advanced patient management system, available from Boston Scientific Corporation, Natick, Mass. Aspects of exemplary in-home monitoring systems are described in U.S. Pat. No. 6,978,182, the content of which is herein incorporated by reference in its entirety.

The external medical device 116 can be configured to detect indicators of system use. Indicators of system use can include, but are not limited to, user input such as through a keyboard, mouse, stylus, or trackball, distance of the implanted medical device relative to the external medical device, presence of a patient in a specific area, such as in a seat adjacent to the external medical device. Distance and position can be determined in various ways such as through the use of GPS functionality, signal strength indicators, and the like. In some embodiments, the external medical device 116 can include a clock circuit in order to track the passage of time. The external medical device 116 can be configured to keep track of the amount of time that has passed since the last indicator of system use was detected.

The external medical device 116 can be configured to take various actions if the amount of time that has passed since the last indicator of system use was detected exceeds a threshold value. For example, the external medical device 116 can be configured to take actions to confirm the identity of the patient and/or take action to conserve the energy of the implanted device. Specifically, the external medical device 116 can be configured to query a system user and/or deactivate one or more transmission features of the implanted medical device 116. In some embodiments, the external medical device 116 can deactivate transmission of real-time data from the implanted medical device 114, deactivate long-range telemetry functionality (such as RF transmission) of the implanted medical device 114, or any combination thereof. In some embodiments, multiple actions to conserve energy can be taken simultaneously. In other embodiments, actions to conserve energy can be taken at different times in a tiered or phased approach.

Figure 2:
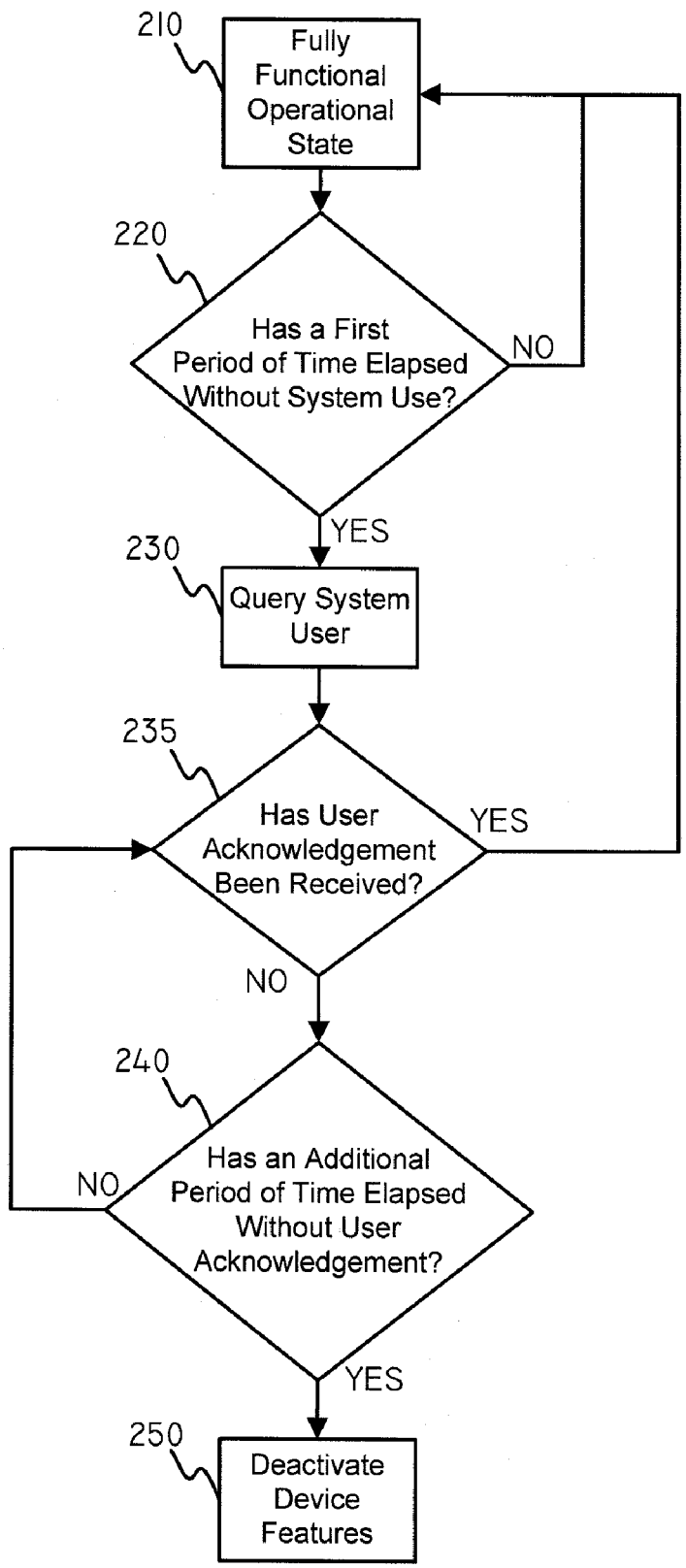
FIG. 2 is a flow diagram in accordance with at least one embodiment of the technology disclosed herein.

FIG. 2 is a flow diagram in accordance with at least one embodiment of the technology disclosed herein. In this embodiment, the implantable medical device starts in a fully functional operational state 210. For example, the implantable medical device would be in a fully functional operational state 210 at the beginning of an interrogation session. In a fully functional operational state 210, the external medical device interrogates the implanted medical device to collect stored data and/or real-time data in addition to sending instructions to the implantable medical device. In the fully functional operational state 210, the RF telemetry functionality of the implanted medical device can be enabled and data can be sent to the external medical device in real-time.

In another operation, the system determines whether a first period of time has elapsed without system use 220. By way of example, the system can determine when the last indicator of system use was registered and whether or not a threshold amount of time has passed since that point in time. Indicators of system use can include any sort of system user input, for example, such as moving a mouse, entering data via a keyboard, or touching the screen on a touch screen device. In another example, indicators of system use can include the distance between the implantable medical device and the telemetry circuit. If the distance is less than some threshold amount, then this can be taken as an indicator of system use. In some embodiments the distance between the implantable medical device and the telemetry circuit, when beyond a threshold amount, serves as a constructive indicator that a period of time has elapsed without system use. In another example, indicators of system use can include a tether-type switch that, when triggered, constructively signifies to the system that a period of time has elapsed without system use 220.

The first period of time or threshold amount of time can be any period of time that would be useful to a medical treatment provider, clinician, or patient. In certain embodiments, the first period of time can range from about 30 seconds to about 30 minutes. In some embodiments, the first period of time can range from about 30 seconds to about 15 minutes. In another embodiment, the first period of time is about 2 minutes.

In some embodiments, the first period of time can be configurable by a system user. In some embodiments, the first period of time can vary depending on the particular data being gathered. Other circumstances can also impact the length of the first time period. For example, if the device interrogation is taking place in conjunction with an implant procedure the first period of time may be longer than if the device interrogation is simply taking place as part of a routine follow-up visit.

In some embodiments, the system can use a self-adjusting timer that starts in response to an indicator of system use, and restarts upon another indicator of system use. In another example, the timer can be ongoing, and the system can be configured to subtract the current time from the time at which there was an indicator of system use in order to determine whether a first period of time has elapsed without system use.

If a first period of time has not elapsed without system use, then the system can return to a fully functional operational state 210. However, if a first period of time has elapsed without system use, the system user is queried 230 in this embodiment. The system can be configured to query a system user regarding whether the session is still pending or the identity of the patient, for example. The system user query can be, for example, a pop-up window requesting confirmation of the patient by the user. In another example, the system can request that the system user enter the name or identifying information of the patient whose implantable medical device is currently being interrogated. In another example, the system can request the user end the current session, continue the current session, start a new session, or any combination thereof.

In another operation, the system can determine whether or not user acknowledgement has been received 235. If user acknowledgement is received, then the system can return to the fully functional operational state 210. However, if a user acknowledgement has not been received, then the system can proceed to determine whether or not an additional period of time, after the first period of time, has elapsed without system use 240. If not, then the system can return to determining whether or not user acknowledgement has been received 235.

The additional period of time can range from about 2 minutes to about 60 minutes beyond the end of the first period of time. In an embodiment, the additional period of time is 13 minutes. The additional period of time can be configurable by the system user, and also can vary depending on the particular data being gathered. Other factors can also determine the length of the additional time period, such as whether the implanted medical device is currently being implanted at the time of interrogation.

In some embodiments, the additional period of time can be configurable by the system user. In some embodiments, the additional period of time can vary depending on the particular data being gathered. Other circumstances can also determine the length of the additional time period. For example, if the medical device is currently being implanted, the additional period of time may be longer than if a routine follow-up visit is taking place.

If an indicator of system use is not recognized or user acknowledgement not received within an additional period of time, the system can deactivate device features 250. The device features can be data transmission features, but are not limited to such. In one embodiment, the system is configured to deactivate real-time data transmission from the implanted medical device after a additional period of time in which one or more indicators of system use are not detected. In another embodiment, the system is configured to deactivate RF transmission of data from the implanted medical device. The system can further be configured to query a system user and/or provide notification to the user of feature deactivation 250.

Figure 3:
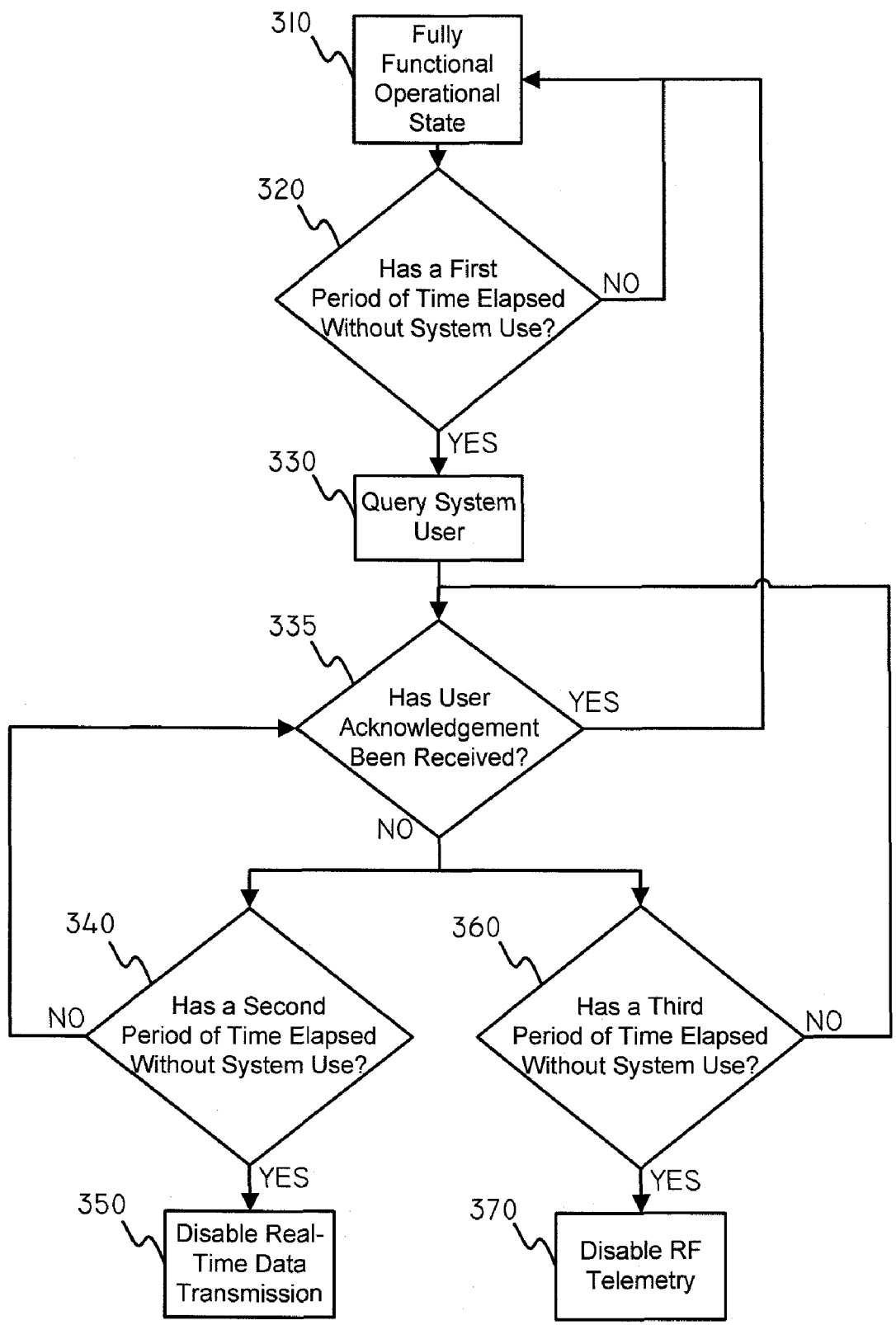
FIG. 3 is a flow diagram in accordance with at least one embodiment of the technology disclosed herein.

In some embodiments, the system can be configured to deactivate features after periods of user inactivity in a phased or tiered manner. By way of example, certain features can be deactivated after a certain period of time while other features can be deactivated after a different period of time. In some embodiments, features that are most energy intensive are deactivated first while other features are deactivated later. FIG. 3 is a flow diagram in accordance with at least one embodiment of the technology disclosed herein. From a fully functional operation state 310, the system determines whether a first period of time has elapsed without system use 320. If so, the system queries the system user 330. If not, the system can return to a fully functional operational state 310.

After querying the system user 330, the system can evaluate whether or not user acknowledgement has been received 335. If user acknowledgement has been received, then the system can return to a fully functional operational state 310. However, if user acknowledgement has not been received, then the system can proceed to evaluate whether a second period of time has elapsed without system use 340. If so, the system deactivates real-time data transmission 350. If not, then the system can return to evaluating whether or not user acknowledgement has been received 335.

In cases where user acknowledgment has not been received, the system can also determine whether a third period of time has elapsed without system use 360. The third period of time can begin after the second period of time has elapsed in some embodiments. In some embodiments, the third period of time can overlap with the second period of time. In other embodiments the third period of time can at least partially overlap with the second period of time, but extend beyond the duration of the second period of time. In at least some embodiments, the third period of time ranges from about 10 minutes to about 2 hours beyond the second period of time. In an embodiment, the third period of time is about 45 minutes.

In some embodiments, the third period of time can be configurable by the system user. In some embodiments, the third period of time can vary depending on the particular data being gathered. Other circumstances can also determine the length of the third period of time. For example, if the medical device is currently being implanted, the third period of time may be longer than if a routine follow-up visit is taking place.

If a third period of time has elapsed without system use and/or user acknowledgement, the system can deactivate long-range telemetry functions of the implanted medical device, such as radio frequency (RF) telemetry 370. In some embodiments long range telemetry functions can be deactivated, and inductive telemetry can be activated. The system can further be configured to query the system user and provide notification to the user of feature deactivation.

FIG. 3 depicts a scenario in which real-time transmission of data is deactivated after a second period of inactivity and RF telemetry is deactivated after a third period of inactivity. However, it will be appreciated that in some embodiments, these deactivations can be reversed in order. In other words, in some embodiments, RF telemetry is deactivated after a second period of inactivity and real-time transmission of data is deactivated after a third period of inactivity. In addition, deactivations of system functionality can include deactivation of features other than RF telemetry and deactivation of real-time transmission of data. In fact, in some embodiments deactivations can extend to all functions of the implanted medical device that are used in conjunction with an interrogation session but that are not used in the ordinary course of operation.

FIG. 2 illustrates a two-phase sequence of operations taken in response to user inactivity. In contrast, FIG. 3 illustrates a three-phase sequence of operations taken in response to user inactivity. It will be appreciated that in various embodiments the number of phases of operations taken in response to user inactivity can be a few as one phase and can be as many as ten phases.

Figure 4:
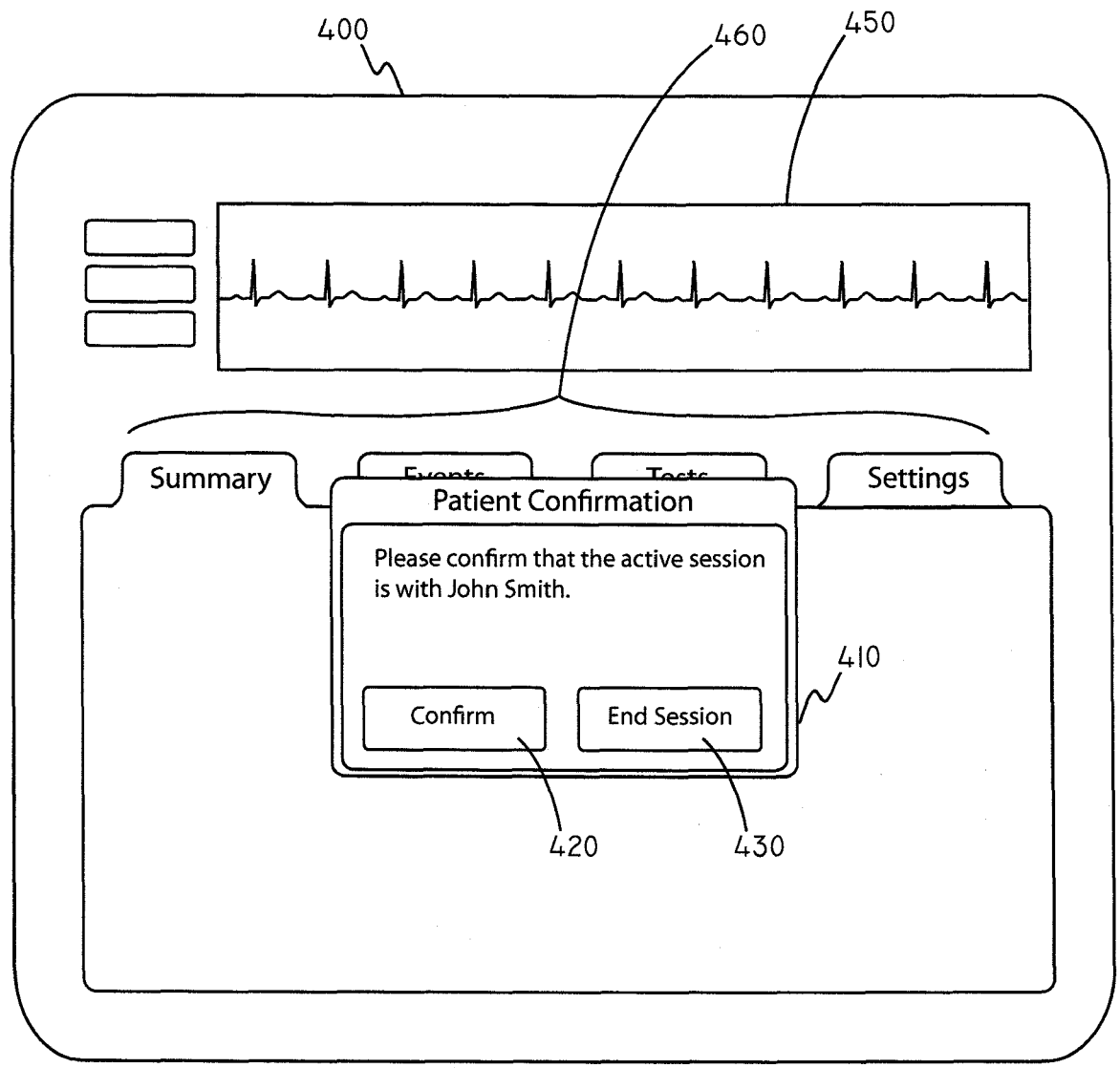
FIG. 4 is an exemplary screen display consistent with at least one embodiment of the technology disclosed herein.

As mentioned above, when the system determines that a first period of time has elapsed without system use, in some embodiments the system can be configured to query the system user. FIG. 4 is an exemplary display screen 400 illustrating an implementation of an exemplary query. In this view, a pop-up window 410 is shown on the display screen 400 having a first button 420 and a second button 430. The pop-up window 410 can serve to query the system user regarding the identity of the patient (John Smith). The first button 420 requests confirmation by the system user of the identity of the patient and the second button 430 provides the system user with the option of ending the session. As an example, the system user could end the session in the event that the patient whose implanted medical device is being interrogated is not John Smith. In another example, a system user could end the session in the event that the interrogation of John Smith's implanted medical device is complete. In some embodiments additional buttons can be provided such as a "new patient" button that can begin a new session for a new patient.

The display screen 400 can include various features such as data 450 from the implanted device. In some embodiments, the data 450 can represent real-time electrogram data. In some embodiments, the data 450 can include graphical data, textual data, or both. The display screen 400 can also include navigational features such as a set of tabs 460 to quickly move between different screens.

Figure 5:
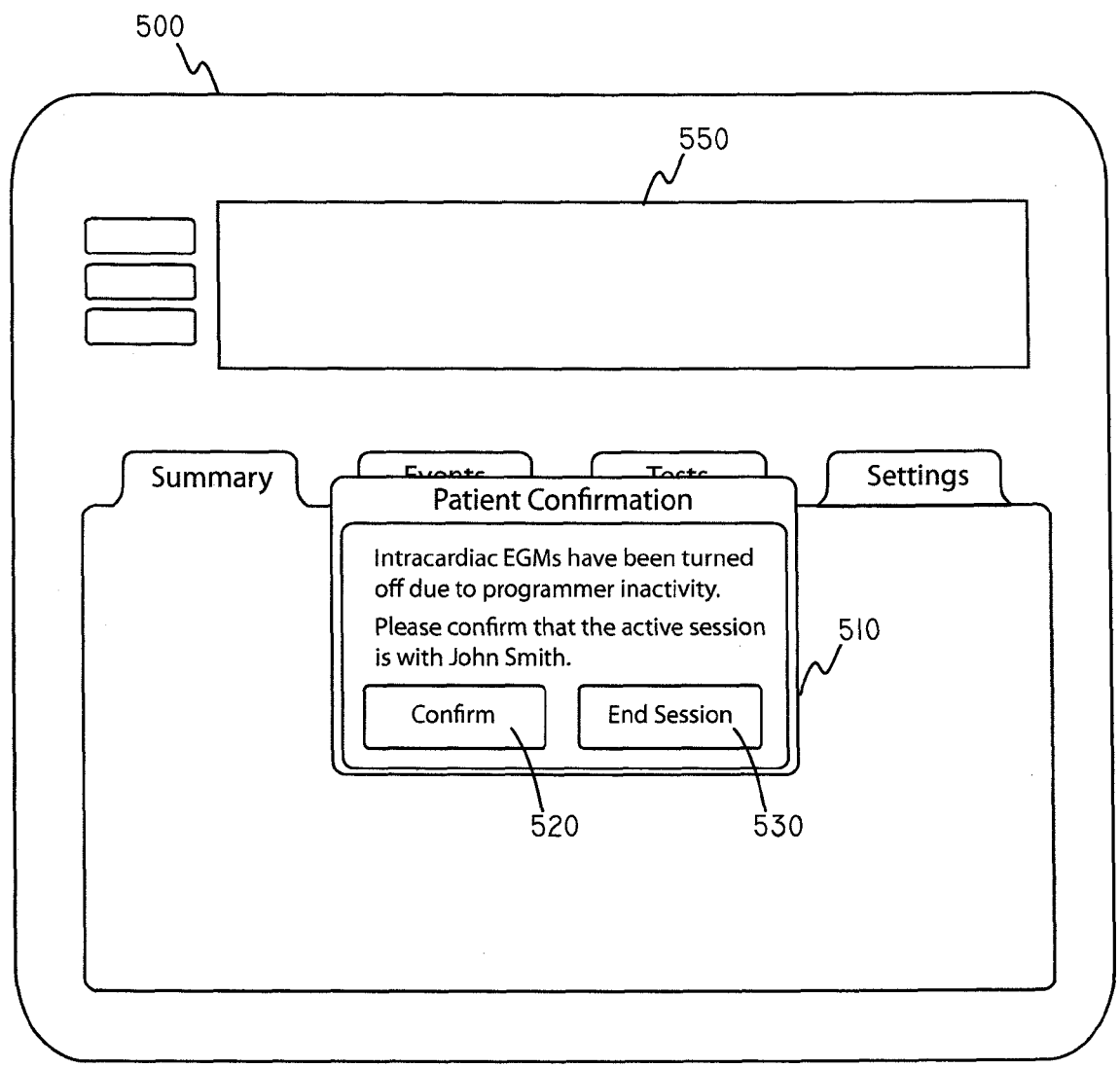
FIG. 5 is an exemplary screen display consistent with at least one embodiment of the technology disclosed herein.

In various embodiments herein, when the system determines that a second or additional period of time has elapsed without system use, the system can deactivate one or more device features with or without also querying the system user. FIG. 5 is an exemplary display screen consistent with at least one embodiment of the technology disclosed herein, wherein the system has determined that a second period of time has elapsed without system use. In this example, real-time electrogram data has been deactivated, and so graphical data 550 is no longer displayed on the screen. The pop-up window 510 notifies system user that the electrogram data has been deactivated. The pop-up window 510 also queries the system user regarding the identity of the patient, providing a first button 520 and a second button 530 to either confirm the patient identity, or end the session, respectively. Additional buttons can also be included.

Figure 6:
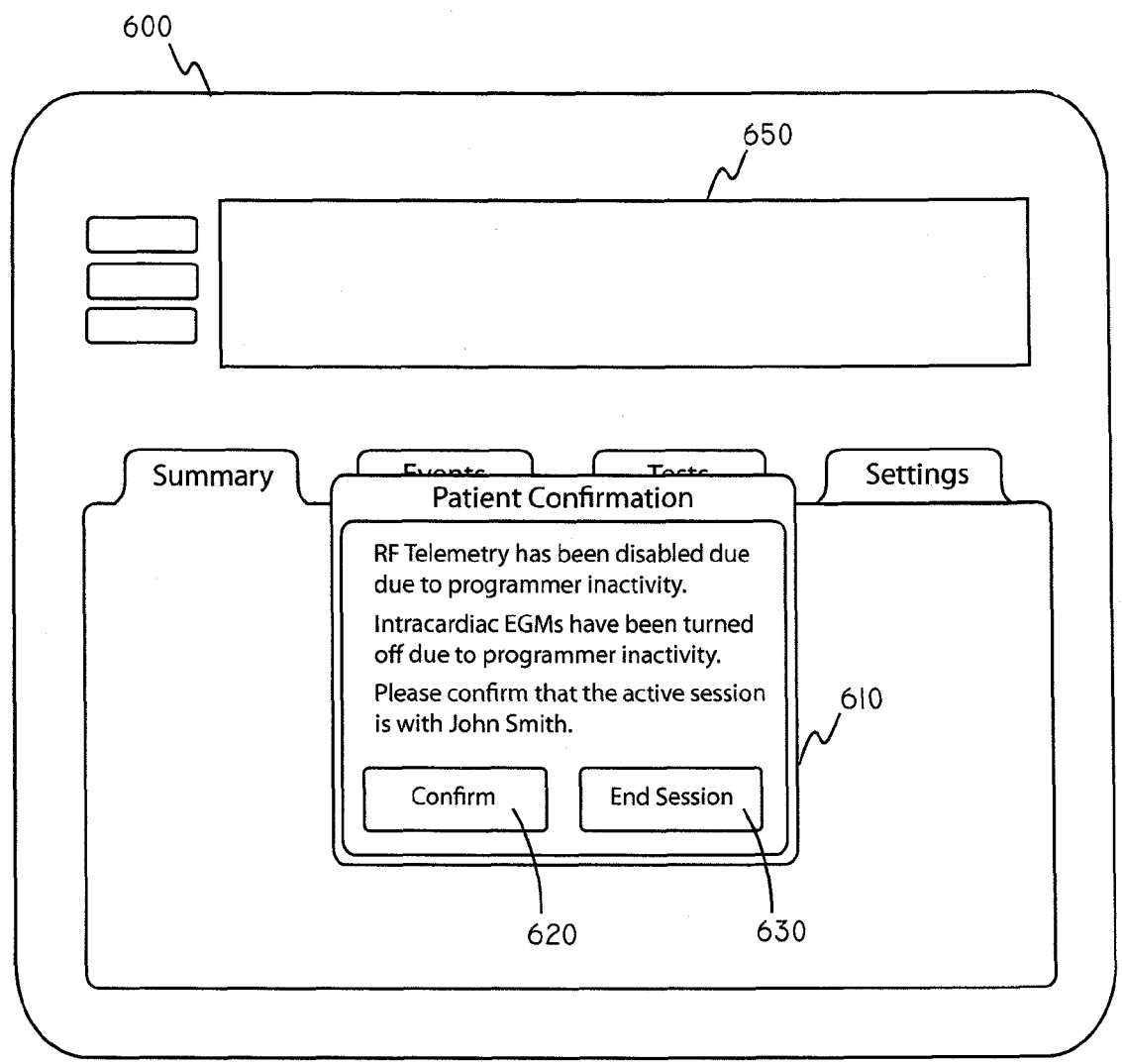
FIG. 6 is an exemplary screen display consistent with at least one embodiment of the technology disclosed herein.

In some embodiments, the system can determine whether or not a third period of time has elapsed without system use. The system response to such a scenario is depicted in FIG. 6, which is an exemplary display screen consistent with at least one embodiment of the technology disclosed herein. In this display screen 600, graphical data 650 and RF telemetry are both deactivated. The pop-up window 610 provides notice of RF telemetry deactivation to the system user. Additionally, the pop-up window 610 notifies the system user that the real-time data transmission has been deactivated. The pop-up window 610 also queries the system user regarding the identity of the patient, providing a first button 620 and a second button 630 to either confirm the patient identity or end the session. Additional buttons can also be included.

Figure 7:
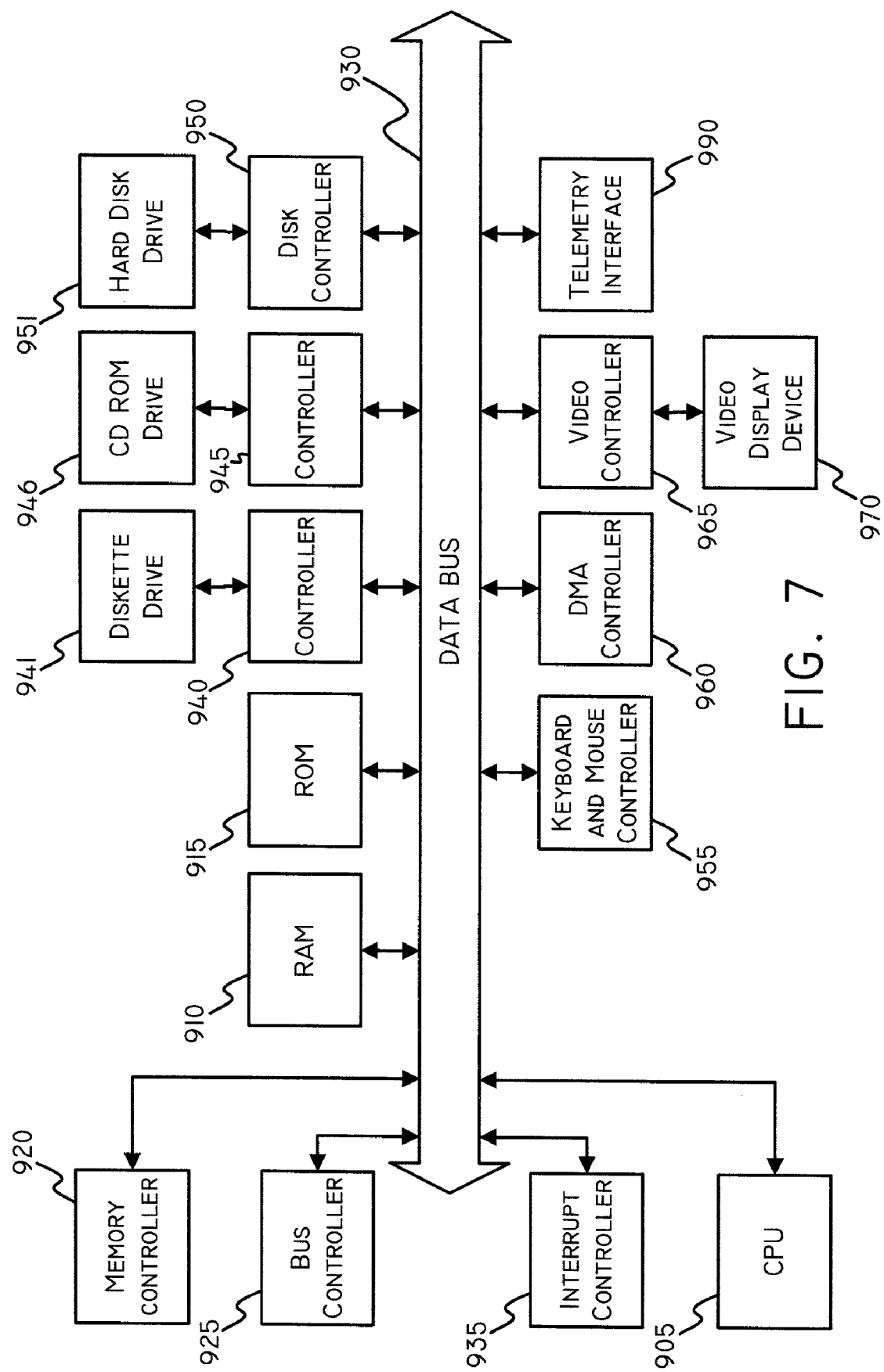
FIG. 7 is a schematic diagram of various external medical system components shown in accordance with at least one embodiment of the technology disclosed herein.

It will be appreciated that external medical systems of various embodiments can include a variety of specific components in order to carry out specific functions and methods as described herein. Referring now to FIG. 7, a diagram of various components that can be included in an external medical system is shown in accordance with an embodiment of the invention. The system includes a central processing unit (CPU) 905 or processor, which may include a conventional microprocessor, random access memory (RAM) 910 for temporary storage of information, and read only memory (ROM) 915 for permanent storage of information. A memory controller 920 is provided for controlling system RAM 910. A bus controller 925 is provided for controlling data bus 930, and an interrupt controller 935 is used for receiving and processing various interrupt signals from the other system components.

Mass storage may be provided by diskette drive 941, which is connected to bus 930 by controller 940, CD-ROM drive 946, which is connected to bus 930 by controller 945, and hard disk drive 951, which is connected to bus 930 by controller 950. User input to the system may be provided by a number of devices. For example, a keyboard and mouse can connected to bus 930 by keyboard and mouse controller 955. DMA controller 960 is provided for performing direct memory access to system RAM 910. A visual display is generated by a video controller 965, which controls video display 970. The system can also include a telemetry interface 990 or telemetry circuit which allows the system to interface and exchange data with an implantable medical device. In will be appreciated that in various embodiments not all of the components depicted in FIG. 7 may be present.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An external medical system comprising:
  a processor; and
  a telemetry circuit in communication with the processor configured to communicate with an implanted medical device;
  a timer in communication with the processor to measure time periods; and
  a video output in communication with the processor;
  the external medical system configured to query a system user through the video output after a first period of time in which indicators of system use are not detected by the processor,
  wherein the first period of time expires prematurely upon detection by the processor of the distance between the implanted medical device and the external medical system exceeding a threshold distance,
  the processor configured to deactivate one or more data transmission features of the implanted medical device after a second period of time in which one or more indicators of system use are not detected.

2. The external medical system of claim 1, the system user query regarding the identity of the patient.

3. The external medical system of claim 1, the indicators of system use comprising system user input.

4. The external medical system of claim 1, the one or more data transmission features comprising transmission of real-time data from the implanted medical device.

5. The external medical system of claim 1, wherein the processor is further configured to deactivate additional data transmission features of the implanted medical device after a third period of time in which indicators of system use are not detected.

6. The external medical system of claim 5, wherein the third period of time ends simultaneously with the end of the second period of time.

7. The external medical system of claim 5, the additional data transmission features comprising long-range telemetry functionality.

8. The external medical system of claim 1, the system configured to deactivate transmission of real-time data from the implanted medical device after a second period of time in which one or more indicators of system use are not detected; and deactivate long-range telemetry functionality of the implanted medical device after a third period of time in which one or more indicators of system use are not detected.

9. The external medical system of claim 1, the first period of time comprising between about 30 seconds and about 30 minutes.

10. The external medical system of claim 1, wherein the second period of time begins after the first period of time has elapsed.

11. The external medical system of claim 1, the second period of time comprising between about 2 minutes and about 60 minutes.

12. The external medical system of claim 1, wherein the third period of time begins after the second period of time has elapsed.

13. The external medical system of claim 1, the third period of time comprising between about 10 minutes and about 2 hours.

* * * * *